US00PP08936P

United States Patent [19]

VandenBerg

[11] Patent Number: Plant 8,936

[45] Date of Patent: Oct. 11, 1994

[54] CHRYSANTHEMUM PLANT NAMED CINDERELLA

[75] Inventor: Cornelis P. VandenBerg, Salinas, Calif.

[73] Assignee: Yoder Brothers, Inc., Barberton, Ohio

[21] Appl. No.: 63,071

[22] Filed: May 18, 1993

[51] Int. Cl.[5] ..... A01H 5/00

[52] U.S. Cl. ..... Plt./80

[58] Field of Search ..... Plt. 76, 80, 81

[56] References Cited

PUBLICATIONS

Sunnyslope Gardens, 1991, "Chrysanthemums '91", San Gabriel, California p. 3.

Sunnyslope Gardens, '85, "Chrysanthemums 1985", San Gabriel, California p. 6.

*Primary Examiner*—Howard J. Locker

*Attorney, Agent, or Firm*—Foley & Lardner

[57] ABSTRACT

A Chrysanthemum plant named Cinderella particularly characterized by its flat capitulum form; decorative capitulum type; light pink ray floret color; diameter across face of capitulum of 64 to 73 mm when fully opened, when grown as a single stem spray cut mum; flowering response in Salinas under normal temperatures is 46 to 53 days after start of short days. Flowering response in bogota, Colombia is 58 to 63 days; plant height is 86 to 94 cm when grown in Salinas with 4 to 18 long days prior to start of short days; height is 104 to 117 cm when grown in Bogota with 14 to 21 long days prior to start of short days; peduncle length of the first lateral at flowering after removing the apical bud without growth regulator applications is 8 to 13 cm when grown in Salinas, and 13 to 15 cm when grown in Bogota; peduncle length of the fourth lateral at flowering is 10 to 15 cm when grown in Salinas, and 18 to 20 cm when grown in Bogota; and excellent tolerance to low night temperatures for bud initiation and flower development.

3 Drawing Sheets

1

The present invention comprises a new and distinct cultivar of Chrysanthemum, botanically known as *Dendranthema grandiflora*, and referred to by the cultivar name Cinderella.

Cinderella, identified as 0989 (90-985001), was originated from a cross made by Cornelis P. VandenBerg in a controlled breeding program in Salinas, Calif., in 1990.

The female parent of Cinderella was the cultivar identified as Momento, disclosed in U.S. Plant Pat. No. 7,407, and described as a flat decorative cut spray mum with a yellow ray floret color; a diameter of capitulum of 64 to 70 mm; a flowering response in Salinas, Calif. of 50 to 54 days; a plant height of 84 to 102 cm when grown with 6 to 14 long days prior to start of short days; a peduncle length of the 1st lateral of 10 to 15 cm and of the 4th lateral of 18 to 20 cm, when grown in Salinas, Calif.; and a terminal spray formation. Momento was never introduced in Colombia, Central America, because of unsatisfactory performance.

The male parent of Cinderella was an unnamed seedling, identified as 1092 (85-245031), and described as a light pink flat decorative cut spray mum with many disc florets; flowering response to short days of 52 to 56 days in Salinas, Calif., and of 65 to 72 days in Bogota, Colombia; a plant height of 64 to 81 cm with 0 to 7 long days prior to start of short days when grown in Salinas, and of 89 to 109 cm with 14 to 15 long days prior to start of short days when grown in Bogota; a peduncle length of the 1st lateral of 10 to 13 cm and of the 4th lateral of 13 to 18 cm, when grown in Salinas, Calif.; a peduncle length of the 1st and the 4th lateral of 10 to 18 cm and 13 to 23 cm when grown in Bogota; a terminal spray formation; and an excellent tolerance to low night temperatures for bud initiation and flower development.

Cinderella was discovered and selected as one flowering plant within the progeny of the stated cross by

2

Cornelis P. VandenBerg in February 1991, in a controlled environment in Salinas, Calif.

The first act of asexual reproduction of Cinderella was accomplished when vegetative cuttings were taken from the initial selection in May 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Cinderella are firmly fixed and are retained through successive generations of asexual reproduction.

Cinderella has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low temperature tolerance was determined in repeated flowerings in Bogota, Colombia, with an average minimum low night temperature inside the greenhouse during our trials ranging as low as 5 to 10 degrees Celsius.

The following traits have been repeatedly observed and are determined to be basic characteristics of Cinderella, which, in combination, distinguish this Chrysanthemum as a new and distinct cultivar:

1. Flat capitulum form.
2. Decorative capitulum type.
3. Light pink ray floret color.
4. Diameter across face of capitulum of 64 to 73 mm when fully opened, when grown as a single stem spray cut mum.

5. Flowering response in Salinas under normal temperatures is 46 to 53 days after start of short days. Flowering response in Bogota, Colombia is 58 to 63 days.

6. Plant height is 86 to 94 cm when grown in Salinas with a 4 to 18 long days prior to start of short days; height is 104 to 117 cm when grown in Bogota with 14 to 21 long days prior to start of short days.

7. Peduncle length of the first lateral at flowering after removing the apical bud without growth regulator applications is 8 to 13 cm when grown in Salinas, and 13 to 15 cm when grown in Bogota. Peduncle length of the fourth lateral at flowering is 10 to 15 cm when grown in Salinas, and 18 to 20 cm when grown in Bogota.

8. Excellent tolerance to low night temperatures for bud initiation and flower development.

The accompanying photographic drawings show typical inflorescence and leaf characteristics of Cinderella, with the colors being as nearly true as possible with illustrations of this type. Sheet 1 is a color photograph of Cinderella grown as a single stem spray cut mum. Sheet 2 is a black and white photograph of three views of the inflorescence of Cinderella. Sheet 3 is a black and white photograph showing the upper and under sides of the leaves of Cinderella at 3 stages of development (mature, intermediate and immature). In sheets 2 and 3 a measuring tape in centimeters has been added.

Of the commercial cultivars known to the inventor, the most similar in comparison to Clnderella is the cultivar identified as Zilcon, disclosed in U.S. Plant Pat. No. 6,052. Reference is made to attached Chart A, which compares certain characteristics of Cinderella with the same characteristics of Zilcon.

Similar traits are capitulum form and type, diameter across face, peduncle length and excellent low night temperatures tolerance. The ray floret color of both Cinderella and Zilcon is light pink. However, the ray floret color of Cinderella is a slightly darker pink than the very light pink ray floret color of Zilcon. Cinderella has a significantly faster flowering response when compared with Zilcon.

In the following description color references are made to the Royal Horticultural Society Colour Chart. The color values were determined on plant material grown as a single stem spray cut mum in Salinas, Calif. on Dec. 15, 1992.

Classification:

*Botanical.*—*Dendranthema grandiflora* cv Cinderella.

*Commercial.*—Decorative spray cut mum.

INFLORESCENCE

A. Capitulum:

*Form.*—Flat.

*Type.*—Decorative.

*Diameter across face.*—64 to 73 mm when fully opened.

B. Corolla of ray florets:

*Color (general tonality from a distance of three meters).*—Light pink.

*Color (upper surface).*—62D.

*Color (under surface).*—65D.

*Shape.*—Straight, oblong, slightly ribbed.

C. Corolla of disc florets:

*Color (mature).*—14A.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—86 to 94 cm when grown in Salinas with 4 to 18 long days prior to start of short days, and 104 to 117 cm when grown in Bogota with 14 to 21 long days prior to start of short days.

B. Foliage:

*Color (upper surface).*—147A.

*Color (under surface).*—147B.

*Shape.*—See photograph.

CHART A

| CULTIVAR | CINDERELLA | ZILCON |
|---|---|---|
| Ray floret color | Light pink | Light pink |
| Capitulum form and type | Flat decorative | Flat decorative |
| Diameter across face of capitulum | 64 to 73 mm | 60 to 80 mm |
| Flowering Response | | |
| in Salinas | 46 to 53 days | 55 to 62 days |
| in Bogota | 58 to 63 days | 68 to 71 days |
| Peduncle length: | | |
| 1st lateral Salinas | 8 to 13 cm | 8 to 13 cm |
| 4th lateral Salinas | 10 to 15 cm | 13 to 20 cm |
| 1st lateral Bogota | 13 to 15 cm | 13 to 15 cm |
| 4th lateral Bogota | 18 to 20 cm | 18 to 23 cm |
| Low night temperature tolerance | Excellent | Excellent |

COMPARISONS MADE OF PLANTS GROWN AS SINGLE STEM SPRAY CUT MUMS IN SALINAS, CALIFORNIA AND IN BOGOTA, COLOMBIA

I claim:

1. A new and distinct Chrysanthemum plant named Cinderella, as described and illustrated.

* * * * *

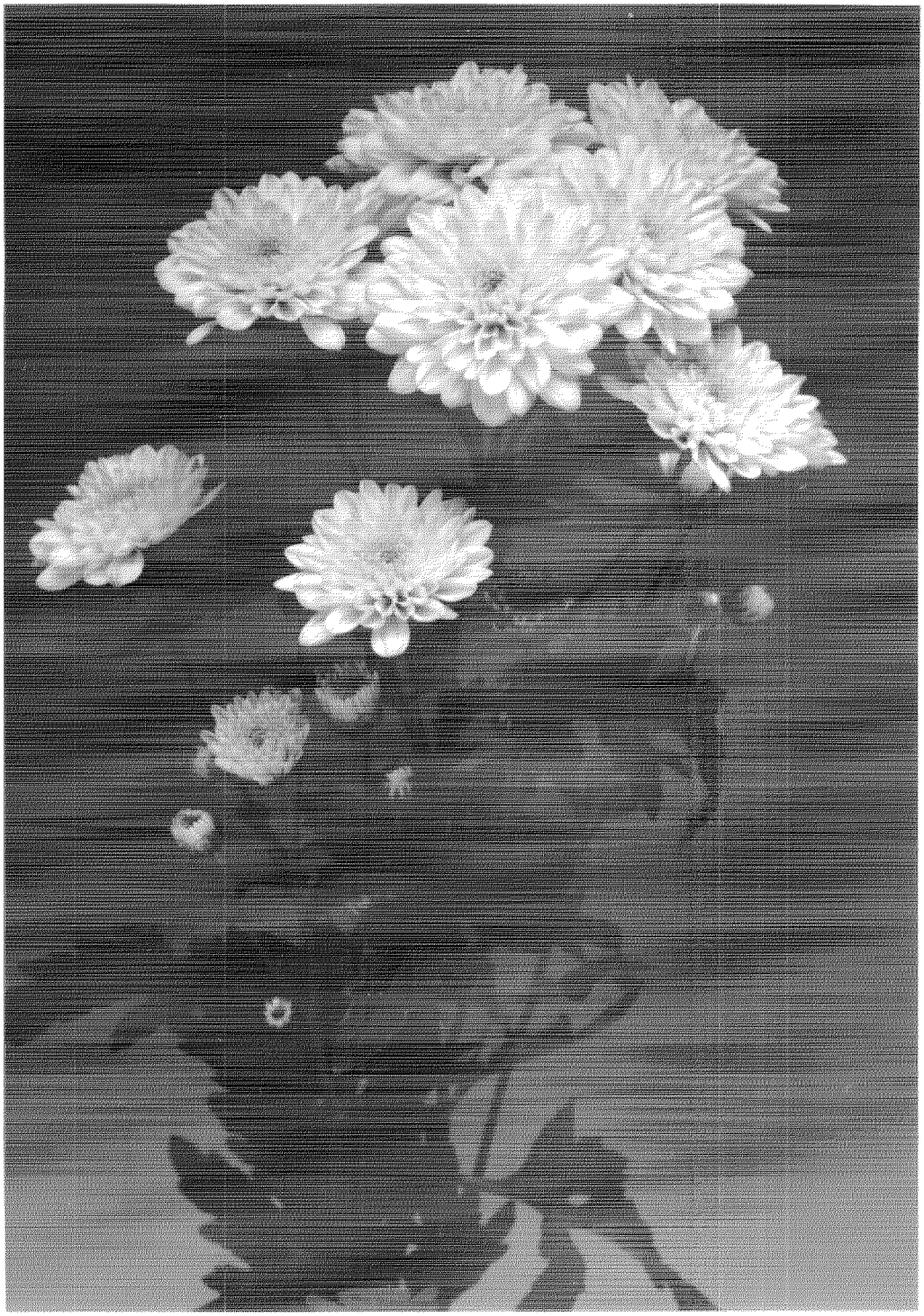

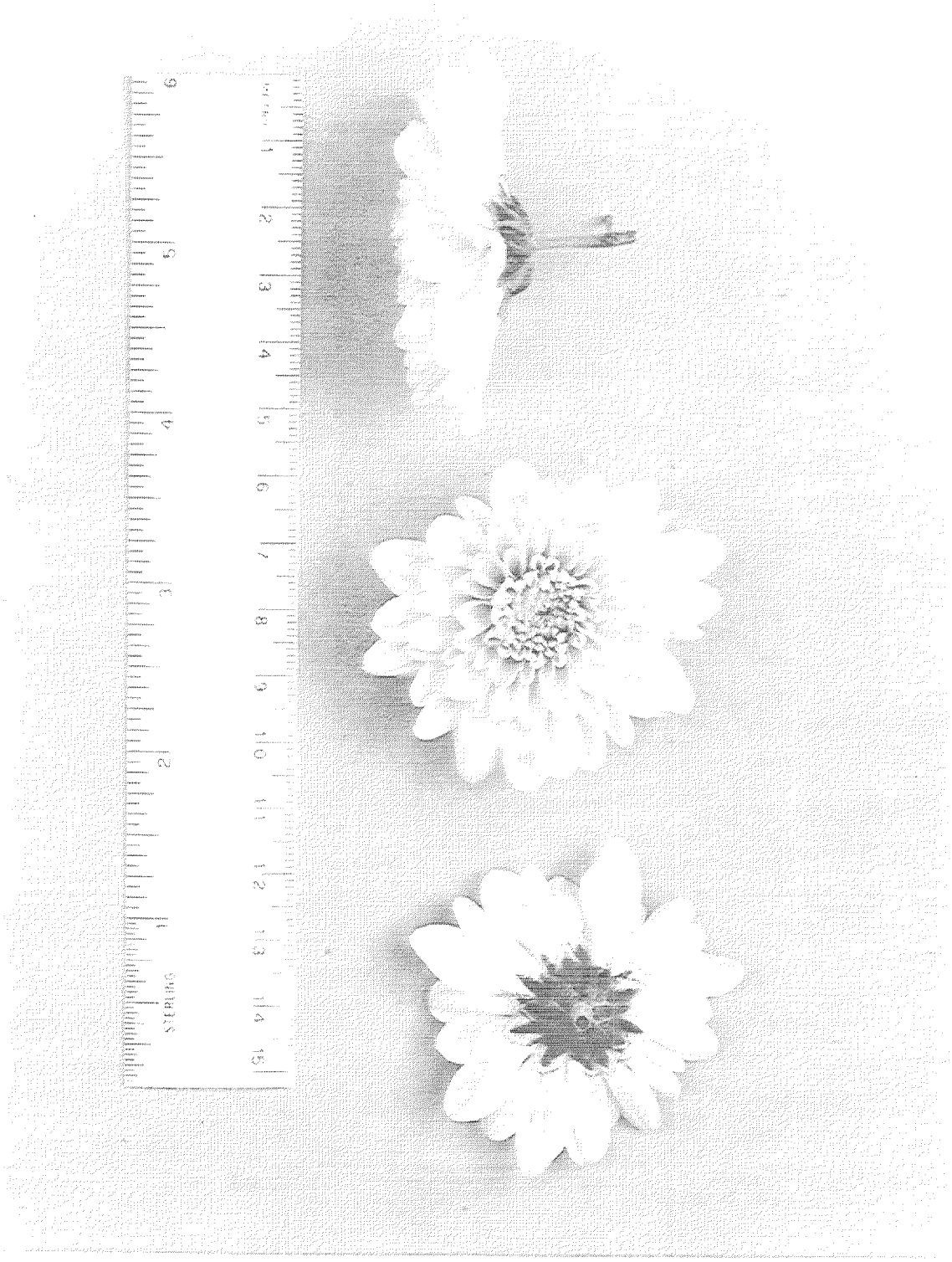
INCHES
1
2
3
4
5
6
CENTIMETERS
1
2
3
4
5
6
7
8
9
10
11
12
13
14
15

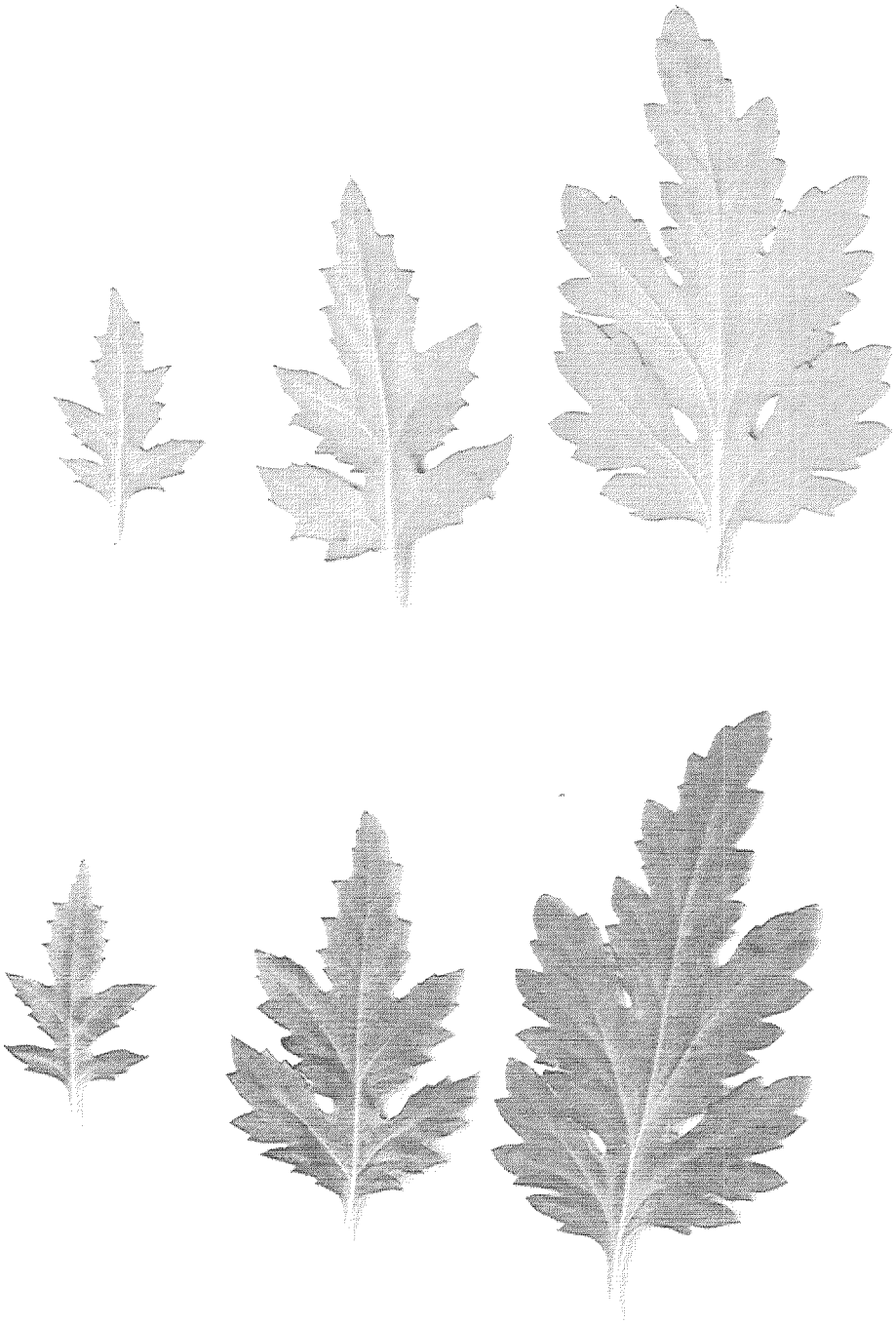

UNITED STATES PATENT AND TRADEMARK OFFICE

CERTIFICATE OF CORRECTION

PATENT NO. : Plant 8,936
DATED : October 11, 1994
INVENTOR(S) : VANDENBERG

It is certified that error appears in the above-indentified patent and that said Letters Patent is hereby corrected as shown below:

On the title page, line 8 of the Abstract, "bogota" should read --Bogota--.

Column 1, line 19, "Central" should read --South--.

Signed and Sealed this

Twenty-third Day of May, 1995

*Attest:*

*Attesting Officer*

BRUCE LEHMAN

*Commissioner of Patents and Trademarks*